United States Patent [19]

Wilhelmi

[11] 4,010,275
[45] Mar. 1, 1977

[54] TREATMENT OF OSTEOARTHRITIS

[75] Inventor: Gerhard Wilhelmi, Reihen, Switzerland

[73] Assignee: Ciba-Geigy Corporation, Ardsley, N.Y.

[22] Filed: Mar. 18, 1975

[21] Appl. No.: 559,608

[52] U.S. Cl. .............................................. 424/285
[51] Int. Cl.² ...................................... A61K 31/34
[58] Field of Search ................................... 424/285

[56] References Cited

OTHER PUBLICATIONS

Chem. Abst., 66–114456w (1967).
Chem. Abst., 69–17874k (1968).
Chem. Abst., 75–18239t (1971).
Chem. Abst.; 73–102,057y (1970).
Chem. Abst.; 66–64001w (1967).

Primary Examiner—Stanley J. Friedman
Attorney, Agent, or Firm—Joseph G. Kolodny; John J. Maitner; Theodore O. Groeger

[57] ABSTRACT

The treatment of Osteoarthritis by orally administering a pharmaceutical preparation containing a furanoside of the formula I

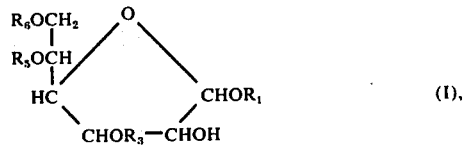

wherein $R_1$ is hydrogen or alkyl with up to 7 carbon atoms, and $R_3$, $R_5$ and $R_6$ each independently is hydrogen, alkyl with up to 7 carbon atoms, alkenyl with up to 7 carbon atoms, benzyl, halogeno-benzyl, ($C_1$-$C_7$-alkyl)-benzyl, ($C_1$-$C_7$-alkoxy)-benzyl or trifluoromethyl-benzyl.

7 Claims, No Drawings

TREATMENT OF OSTEOARTHRITIS

DESCRIPTION OF THE INVENTION

The invention relates to the treatment of osteoarthritis (arthrosis) which is characterized by orally administering a pharmaceutical preparation containing a furanoside of the formula I

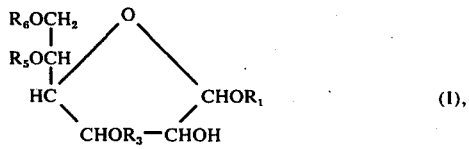

wherein $R_1$ is hydrogen or alkyl with up to 7 carbon atoms, and $R_3$, $R_5$ and $R_6$ each independently is hydrogen, alkyl with up to 7 carbon atoms, alkenyl with up to 7 carbon atoms, benzyl, halogeno-benzyl, ($C_1$-$C_7$-alkyl)-benzyl, ($C_1$-$C_7$-alkoxy)-benzyl trifluoromethyl-benzyl.

A residue $R_1$, $R_3$, $R_5$, and $R_6$ being alkyl with up to 7 carbon atoms and $C_1$-$C_7$-alkyl in a residue $R_3$, $R_5$ and $R_6$ being ($C_1$-$C_7$-alkyl)-benzyl is methyl, ethyl, propyl or isopropyl, and straight or branched butyl, pentyl, hexyl or heptyl bonded in any desired position.

A residue $R_3$, $R_5$ and $R_6$ being alkenyl with up to 7 carbon atoms is especially for example an allyl and methallyl radical.

Halogen in a halogeno-benzyl radical $R_3$, $R_5$ and $R_6$ is fluorine, bromine, iodine and especially chlorine.

$C_1$-$C_7$-alkoxy in a residue $R_3$, $R_5$ and $R_6$ being ($C_1$-$C_7$-alkoxy)-benzyl is ethoxy, n-propoxy, iso-propoxy and straight or branched butyloxy, pentyloxy, hexyloxy or heptyloxy and especially methoxy.

Substituted benzyl radicals have the substituent preferably in para position.

The compounds of the formula I are mixtures of anomers or $\alpha$- or $\beta$-anomers.

It has been found that orally administering a pharmaceutical preparation as defined above is helpful for the treatment of osteoarthritis. This can be shown by the following test, wherein male mice (strain C 57 black with a certain incidence of spontaneous osteoarthritis) of an age of 13 to 15 and 15 to 18 months were divided in to two groups, one receiving the furanoside (e.g. ethyl-3,5,6-tri-O-benzyl-D-glucofuranoside) in sterile olive oil and the other the same quantity of sterile olive oil for three months. Then the mice were killed, the hind leg radiographed and the knee-joints inspected histologically. This test gave the following results:

According to a preferred embodiment of the invention the treatment of osteoarthritis is performed by orally administering a pharmaceutical preparation containing a compound of the formula I, wherein $R_1$ is alkyl with up to 4 carbon atoms, and $R_3$, $R_5$ and $R_6$ each independently is alkyl with up to 4 carbon atoms, alkenyl with up to 4 carbon atoms, benzyl, halogeno-benzyl, ($C_1$-$C_4$-alkyl)-benzyl, ($C_1$-$C_4$-alkoxy)-benzyl or trifluoromethyl-benzyl.

Above all to be mentioned is said treatment using a pharmaceutical preparation containing a compound of the formula I, wherein $R_1$ is alkyl with up to 4 carbon atoms, especially methyl or ethyl, and one, two or all three of $R_3$, $R_5$ and $R_6$ are benzyl, chloro-benzyl, methyl-benzyl, methoxy-benzyl or trifluoromethyl-benzyl and the remaining are alkyl with up to 4 carbon atoms or alkenyl with up to 4 carbon atoms, especially methyl, ethyl, n-propyl or allyl.

Compounds of the formula I to be especially highlighted are ethyl-3-O-n-propyl-5,6-di-O-(4-chlorobenzyl)-D-glucofuranoside and above all ethyl-3,5,6-tri-O-benzyl-D-glucofuranoside.

According to the invention the pharmaceutical preparations as defined above are administered orally to a warm-blooded animal in doses sufficient for improving or preventing arthrosis. Thus, a warm-blooded animal of about 75 kg body weight is orally treated with a daily dose of about 400 mg to about 1200 mg, above all of about 600 mg to about 1200 mg of a compound of the formula I, especially one of the above preferably mentioned compounds of the formula I. The compound of the formula I is preferably administered in the form of a pharmaceutical preparation.

According to a preferred method of treatment of arthrosis a pharmaceutical preparation is orally administered containing as compound of the formula I ethyl-3-O-n-propyl 5,6-di-O-(4-chlorobenzyl)-D-glucofuranoside or ethyl-3,5,6tri-O-benzyl-D-glucofuranoside in doses of about 400 mg to about 1200 mg, especially of about 600 mg to about 1200 mg per day of said compounds of the formula I.

The pharmaceutical preparations contain a compound of the formula I either without any carrier or preferably in admixture or conjunction with a pharmaceutically acceptable carrier for liquid or solid preparations.

A pharmaceutically acceptable carrier is for example concentrated milk, a suitable oil, such as olive oil, polyethyleneglykole or carboxymethylcellulose. Such a pharmaceutically acceptable carrier is especially suitable for liquid pharmaceutical preparations.

A pharmaceutically acceptable carrier especially suitable for solid pharmaceutical preparations is for

| group | age | number of animals | dosis mg/kg/ week | Arthrosis found without incipi- ences* in % | | with incipi- ences in % | | protection against arthrosis in % |
|---|---|---|---|---|---|---|---|---|
| 1 | 13–15 | 31 | 500 | 12 | 38.7 | 12 | 38.7 | 36 |
| 2 | 13–15 | 28 | 0 | 17 | 60.7 | 18 | 64.3 | |
| 3 | 15–18 | 26 | 1200 | 4 | 15.4 | 8 | 30.8 | 60 |
| 4 | 15–18 | 26 | 0 | 10 | 38.5 | 17 | 65.4 | |

*as incipience there was taken the incidence of fraying of the cartilaginous surface in the knee. An assay with mice having an age of 12 to 13 months showed a similar protection against arthrosis, when the animals were treated by 150 mg/kg weekly for three months.

example described in U.S. Pat. No. 3,594,474. Accordingly, a free flowing granular material which can easily be processed into solid oral administration forms can be obtained in a simple manner if an oily or liquid compound of the formula I is mixed with a film-forming agent and a lower alkanol such as methanol, isopropanol or primarily ethanol, worked into a plastic mass with magnesium trisilicate, if desired together with a further adsorbent such as colloidal silica or cellulose, especially microcrystalline cellulose, and the mass granulated whilst drying it, for example with warm air.

As film-forming agents there are preferably used those which also act as binding agents, especially shellac, poly-acrylic or methacrylic derivatives, especially their esters, carbowaxes, polyvinyl derivatives such as polyvinyl acetates, or primarily polyvinyl pyrrolidones, for example polyvinylpyrrolidone or polyvinylpyrrolidone-polyvinyl acetate copolymers. Further possible film-forming agents are alcohol-soluble or water-soluble cellulose derivatives, especially cellulose acetate-phthalate, hydroxypropyl-methylcellulose, ethylcellulose, ethyl-hydroxyethyl-cellulose, hydroxypropyl-cellulose, carboxymethylcellulose and/or carboxyethylcellulose.

The process is preferably effected by dissolving the film-forming agent in the lower alkanol, mixing the furanoside with this solution, and mixing this solution with the magnesium trisilicate and optionally the adsorbent to give a plastic mass, and drying and granulating the latter in the usual manner. When mixing the solution of the furanoside with magnesium trisilicate, the sugar is adsorbed on the latter.

The film-forming agent is preferably used in a concentration of 0,2 to 20, especially 1-5 and primarily 2-4, parts by weight relative to 10 parts by weight of furanoside. The magnesium trisilicate is used in an amount which permits adsorption of the furanoside, especially in a concentration of 5-20, preferably 8-15 or primarily about 10-12 parts by weight calculated relative to 10 parts by weight of furanoside. The further adsorbent is used in an amount of 1-20, preferably 1-10 and primarily 4-6, parts by weight calculated relative to 10 parts by weight of furanoside.

The granular material obtained is stable for prolonged periods even at a higher temperature, for example 60°, and can be easily processed into any desired oral administration form.

The granular material is suitable for the manufacture of solid oral administration forms such as tablets, push-fit capsules or primarily dragées. These may be obtained in the usual manner.

EXAMPLE 1

10 parts by weight of ethyl-3,5,6-tri-O-benzyl-D-glucofuranoside, 10 parts by weight of magnesium trisilicate, 5 parts by weight of colloidal silica and 2.5 parts by weight of polyvinylpyrrolidone (PVP).

The PVP is dissolved in a fourfold amount of alcohol and mixed with the ethyl-3,5,6-tri-O-benzyl-D-glucofuranoside. This solution is processed into a paste with the magnesium trisilicate in a suitable apparatus and is kneaded with colloidal silica to give a plastic mass. It is then granulated and dried in the usual manner.

5.45 parts by weight of granular material are mixed with 2.0 parts by weight of starch, 1.7 parts by weight of talc and 0.3 part by weight of magnesium stearate and processed into pressed blanks weighing 585 mg and containing 200 mg of ethyl-3,5,6-tri-O-benzyl-D-glucofuranoside.

In order to mask the bad taste, the pressed blanks are, after coating with a protective lacquer, converted in the usual manner with sugar into dragées.

The daily oral dose for a warm-blooded animal of about 75 kg body weight is about 2 to 6 dragées.

EXAMPLE 2

10 parts by weight of preparation of ethyl-3-O-n-propyl-5,6-di-O-p-chlorobenzyl-D-glucofuranoside, 14 parts by weight of magnesium trisilicate, 5 parts by weight of colloidal silica and 2.5 parts by weight of polyvinylpyrrolidone.

The PVP is dissolved in the fourfold quantity of alcohol and mixed with the furanoside. This solution is processed into a paste with magnesium trisilicate in a suitable apparatus and kneaded with colloidal silica to give a plastic mass. The mass is granulated and dried in the usual manner.

31.5 parts be weight of granular material are mixed with 0.8 part by weight of starch, 1.55 parts by weight of microcrystalline cellulose, 1.05 parts by weight of talc and 0.15 part by weight of magnesium stearate and processed into pressed blanks of 350 mg=100 mg of furanoside.

These cores are given a protective lacquer in the usual manner and then converted into dragées with sugar.

The daily oral dose for a warm-blooded animal of about 75 kg body weight is about 6–12 dragées.

EXAMPLE 3

10 parts by weight of ethyl-3,5,6-tri-O-benzyl-D-glucofuranoside, 10 parts by weight of magnesium trisilicate, 5 parts by weight of colloidal silica, 0.5 part by weight of polyvinylpyrrolidone, and 2 parts by weight of microcrystalline cellulose.

The PVP is dissolved in a fourfold amount of alcohol and mixes with the ethyl-3,5,6-tri-O-benzyl-D-glucofuranoside. This solution is processed into a paste with the magnesium trisilicate in a suitable apparatus and is kneaded with colloidal silica to give a plastic mass. It is then granulated and dried in the usual manner.

5.45 parts by weight of granular material are mixed with 2.0 parts by weight of starch, 1.7 parts be weight of talc and 0.3 part by weight of magnesium stearate and processed into pressed blanks weighing 585 mg and containing 200 mg of ethyl-3,5,6-tri-O-benzyl-D-glucofuranoside.

In order to mask the bad taste, the pressed blanks are, after coating with a protective lacquer, converted into dragees with sugar in the usual manner.

The daily oral dose for a warm-blooded animal of about 75 kg body weight is about 6–12 dragées.

What is claimed is:

1. A method of treatment of osteoarthritis which is characterized by orally administering to warm-blooded animals a pharmaceutical preparation containing a therapeutically effective amount of a furanoside of the formula I

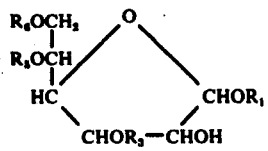

(I), wherein $R_1$ is hydrogen or alkyl with up to 7 carbon atoms, and $R_3$, $R_5$ and $R_6$ each independently is hydrogen, alkyl with up to 7 carbon atoms, alkenyl with up to 7 carbon atoms, benzyl, halogeno-benzyl, ($C_1$-$C_7$-alkyl)-benzyl, ($C_1$-$C_7$-alkoxy)-benzyl or trifluoromethyl-benzyl.

2. A method as claimed in claim 1, wherein a compound of the formula I is used, wherein $R_1$ is alkyl with up to 4 carbon atoms, and $R_3$, $R_5$ and $R_6$ each independently is alkyl with up to 4 carbon atoms, alkenyl with up to 4 carbon atoms, benzyl, halogeno-benzyl, ($C_1$-$C_4$-alkyl)-benzyl, ($C_1$-$C_4$-alkoxy)-benzyl or trifluoromethyl-benzyl.

3. A method as claimed in claim 1, wherein a compound of the formula I is used, wherein $R_1$ is alkyl with up to 4 carbon atoms, and one, two or all three of $R_3$, $R_5$ and $R_6$ are benzyl, chloro-benzyl, methyl-benzyl, methoxy-benzyl or trifluoromethyl-benzyl and the remaining are alkyl with up to 4 carbon atoms or alkenyl with up to 4 carbon atoms.

4. A method as claimed in claim 1, wherein a compound of the formula I is used, which is ethyl-3O-n-propyl-5,6-di-O-(4-chlorobenzyl-D-glucofuranoside.

5. A method as claimed in claim 1, wherein a compound of the formula I is used, which is ethyl-3,5,6-tri-O-benzyl-D-glucofuranosid.

6. A method as claimed in claim 1, wherein a compound of the formula I is used in a daily dose of 400–1200 mg in a warm-blooded animal of about 75 kg body weight.

7. A method as claimed in claim 1, wherein the pharmaceutical preparation contains a compound of the formula I in admixture or conjunction with a pharmaceutically acceptable carrier.

* * * * *